United States Patent [19]

Stekolnikov et al.

[11] 4,195,097

[45] Mar. 25, 1980

[54] METHOD FOR PREPARING ENZYMAYTIC COMPOSITION FOR ACCELERATION OF AGEING OF MEAT PRODUCTS

[75] Inventors: Leonid I. Stekolnikov; Boris A. Sevastyanov, both of Moscow; Gennady G. Shilov, Rostov-na-Donu; Anatoly A. Belousov, Moscow; Nikolai D. Mamonov, Rostov-na-Donu, all of U.S.S.R.

[73] Assignee: Vsesojuzny Nauchno-Issledovatelsky Institut Myasnoi Promyshlennosti, Moscow, U.S.S.R.

[21] Appl. No.: 884,540

[22] Filed: Mar. 8, 1978

[30] Foreign Application Priority Data

Mar. 14, 1977 [SU] U.S.S.R. .............................. 2464202

[51] Int. Cl.$^2$ .................... A22C 11/00; A23P 1/00; A23L 1/31
[52] U.S. Cl. .................................... 426/61; 426/56; 426/59; 426/641; 426/646
[58] Field of Search ............... 426/56, 58, 59, 61, 426/641, 646; 195/68, 63, 29.4

[56] References Cited

FOREIGN PATENT DOCUMENTS 471885 8/1975 U.S.S.R. ................................... 426/56

OTHER PUBLICATIONS

Colowick et al., "Methods in Enzymology", vol. 1, Academic Press, N.Y., N.Y. 1955, pp. 166–173.

*Primary Examiner*—S. Leon Bashore
*Assistant Examiner*—William F. Smith
*Attorney, Agent, or Firm*—Fleit & Jacobson

[57] ABSTRACT

The invention relates to a method for preparing an enzymatic composition for acceleration of ageing of meat products involving a separate dissolution of an enzyme, viz. hyaluronidase and a prolongator of biological effect, viz. serum albumin at a pH value of from 2.0 to 2.5; hyaluronidase is taken in an amount of from 4 to 6 parts by weight and serum albumin in an amount of from 0.5 to 1.5 part by weight. Said aqueous solution of the enzyme is mixed with said aqueous solution of the prolongator, whereupon said ingredients chemically react with each other to give a suspension comprising a mixture of an aqueous solution of the desired product with suspended particles of the unreacted ingredients. After mixing of the aqueous solutions, the desired product is isolated by separation of the aqueous solution thereof from particles of the unreacted ingredients and precipitation of the desired product from said aqueous solution by means of an organic solvent at a volumetric ratio between said solvent and the solution of 4–10:1; the aqueous solution is previously cooled to a temperature of 4°–6° C.; the precipitate of the desired product is then separated from the liquid phase and dried in succession with acetone and ethyl ether. The enzymatic composition prepared according to the present invention has certain advantages over the prior art compositions employed for treatment of meat products. It is stable upon long-term storage and retains its activity unchanged at 18°–20° C. for 2 years and longer.

9 Claims, No Drawings

METHOD FOR PREPARING ENZYMATIC COMPOSITION FOR ACCELERATION OF AGEING OF MEAT PRODUCTS

FIELD OF THE INVENTION

The present invention relates to methods for preparing enzymatic compositions intended for acceleration of ageing of meat products. The enzymatic composition according to the present invention is useful in meat production and public catering.

BACKGROUND OF THE INVENTION

Known in the art are methods for preparing enzymatic compositions for the treatment of meat products, viz. bromeline and bromelaine from pineapples an enzymatic composition from sprouted seeds of soya, ficine from a fig latex, enzymatic agent papain.

The prior art enzymatic agents feature certain disadvantages which in some cases reside in high costs and unavailability of the starting materials, and in other cases in instability of the final enzymatic compositions upon longtime storage. Furthermore, some of the above-mentioned enzymatic agents (such as that produced from sprouted soya seeds) impart a foreign odor to the meat products being treated; they become inoculated with microflora and, on the whole, provide but an insignificant effect.

Also known in the art is a method of preparing an activated enzymatic agent from the pancreas for acceleration of maturation of meat products which comprises defatting the pancreas of slaughter animals, disintegration, cuttering and autolysis at the temperature of 40° C., followed by mixing of the autolyzate with prolongators of the biologic effect, whereafter the resulting mixture is extracted with water, grist is separated by filtration and then again extracted with water; the grist remaining after the second extraction being again separated by filtration. The liquors after extraction are combined and added with prolongators of the biologic effect; the resulting mixture is subjected to a sterilizing filtration and dispensed into sterile containers.

This prior art method for the preparation of an enzymatic agent resides in a complicated and time-consuming process technology as well as producing a foul odour and limited period of action; moreover, it insufficiently softens tough parts of meat.

SUMMARY OF THE INVENTION

It is an object of the present invention to select such starting enzyme and prolongator which would make it possible to prepare an enzymatic composition stable upon storage and possessing a prolonged specific effect.

This object is accomplished by a method for preparing an enzymatic composition for acceleration of ageing of meat products involving mixing of an enzyme with a biological-effect prolongator and separating the desired product, wherein, in accordance with the present invention as the enzyme use is made of hyaluronidase, while as the biological-effect prolongator use is made of serum albumin; prior to mixing said enzyme with said prolongator these are separately dissolved in water at a pH of 2.0 to 2.5; hyaluronidase is employed in an amount of from 4 to 6 parts by weight and serum albumin is taken in an amount of from 0.5 to 1.5 part by weight; as a result of intermixing of aqueous solutions of hyaluronidase and serum albumin said ingredients enter into a chemical interaction to give a suspension comprising a mixture of an aqueous solution of the desired product with suspended particles of the unreacted ingredients. After mixing of said aqueous solutions the desired product is isolated in the following manner. The aqueous solution of the desired product is separated from the particles of the unreacted ingredients and the desired product is then precipitated from said aqueous solution by means of an organic solvent at a volumetric ratio between said solvent and solution of from 4:1 to 10:1 respectively; in doing so, said aqueous solution and the organic solvent are preliminary cooled to a temperature of from 4° to 6° C., then the precipitate of the desired product is separated from the liquid phase and successively dried with acetone and ethyl ether.

The method according to the present invention is performed in the following manner.

DETAILED DESCRIPTION OF THE INVENTION

The method according to the present invention is embodied in the following manner.

Preliminary prepared are solutions of hyaluronidase and serum albumin, the solutions being prepared separately. Dissolution of said compounds is effected in water at a pH of from 2.0 to 2.5 and at a temperature of 18° to 20° C. Hyaluronidase is taken for dissolution in an amount of from 4 to 6 parts by weight and serum albumin in an amount of from 0.5 to 1.5 part by weight. These proportions of the components ensure optimal conditions of interaction of said compounds.

Serum albumin per se does not possess an enzymatic activity and provides no effect on the quality of meat products. However, when added to an enzyme, i.e. hyaluronidase in accordance with the present invention, it is capable of reacting therewith, since serum albumin is rather a high-molecular protein (its molecular weight is about 65,000) containing in its molecule reactive groups such as $-NH_2$, $-COOH$ and the like. This reaction gives a complex compound, wherein labile active centers of the enzyme are protected from the destroying effect of factors of the ambient medium (light, humidity and the like) which ensures manifestation of a specific hyaluronidase activity for a period much longer than that of the native enzyme.

Intermixing of aqueous solutions of hyaluronidase and serum albumin is effected at a temperature within the range of from 18° to 20° C. for a period of from 1 to 2 hours. To separate particles of the unreacted ingredients, the suspension resulting from intermixing of said aqueous solutions is filtered, the precipitate containing the unreacted ingredients is discarded. The filtrate containing a water-soluble complex of hyaluronidase and serum albumin is cooled to a temperature of from 4° to 6° C. The cooled solution is poured, in a thin stream, under vigorous stirring into an organic solvent preliminarily cooled to a temperature of not more than 10° C., preferably from 2° to 4° C., at a volumetric ratio between said solvent and solution ranging from 4:1 to 10:1 respectively.

As the organic solvent it is preferable to use acetone, ethylacetate, ethanol or other monohydric alcohols. The resulting precipitate is separated by centrifugation or filtration, while the mother liquor is recycled to regeneration. The crude precipitate containing the enzymatic composition is dried by way of repeated washing with acetone and then with ether, followed by post-drying in the air to completely eliminate the solvent odor. The resulting enzymatic composition comprises an amorphous powder of white or white-yellowish colour and with a slightly pronounced specific odor of raw meat. Pharmaceutical and biological investigations have proven that this enzymatic composition exerts no detrimental effect at all on animal organisms.

Meat or meat products are treated with the thus-prepared enzymatic composition at a rate of from 0.05 to 2% by weight of the meat using either wet or dry method as well as by means of injection of a solution of the composition. After 3 to 6 hours there is observed a noticeable increase (by 15 to 20%) of the water-retaining ability and softness of samples as compared to untreated meat; there is also observed accumulation of free aminoacids and microstructural changes in muscular tissue which demonstrates acceleration of the biochemical processes of meat ageing. Upon keeping of untreated meat or meat products at the temperature of 2° C. the properties similar to those mentioned hereinabove are achieved only after 10-12 days of storage which shows that processes of meat ageing with the use of the enzymatic composition according to the present invention are accelerated by 10 to 20 times.

The use of the enzymatic composition prepared by the method according to the present invention for the treatment of meat products has a number of advantages over other enzymatic agents employed for the same purpose. This composition is stable upon a long-time storage and does not lose its activity at a temperature of from 18° to 20° C. for two years. Furthermore, this enzymatic composition of the present invention has a specific effect of splitting hyaluronic acid incorporated in a connective tissue; it also activates natural proteinases of a muscular tissue which, in turn, exert a hydrolizing effect on actomyosin and other muscular proteins which, as a result, accelerates digestion of meat and increases the biological effect thereof.

For a better understanding of the present invention some specific Examples illustrating the method for preparing an enzymatic composition are given hereinbelow.

EXAMPLE 1

1 g of ox serum albumin containing at most 10% by weight of water and at least 85% by weight of soluble protein compounds is dissolved in 100 mol of water acidified with a 0.5 N HCl to a pH of 2.0. 5 g of hyaluronidase with an activity of 64 units in 100 mg of dry powder are separately dissolved in 100 ml of water acidified to a pH of 2.0 and this solution is slowly poured into the solution of serum albumin, intermixed at a temperature of from 18° to 20° C. for 60 minutes, whereafter it is filtered through a Büchner funnel or paper filters to separate a small amount of the unreacted starting ingredients. The filtrate is cooled to the temperature of 4° C. and poured in a thin jet under stirring into 4 volumes of acetone cooled to the temperature of 4° C. The mixture is stirred for 5 minutes and allowed to stay for 4 hours at 4° C. The liquid over the precipitate is separated by decantation, while the precipitate with the remaining amount of the liquid is subjected to centrifugation at the speed of 3,000 r.p.m. for 10 minutes and then washed repeatedly with acetone (25-30 ml of acetone per each washing) and with ether (with portions of 25 ml) and post-dried in the air to eliminate the solvent odor. There are obtained 5.52 g of an amorphous powder (the yield is equal to 92%) having no odor and with a light-yellow color; it is readily soluble in water at a pH of from 2.0 to 8.5 and insoluble in ethanol, acetone, ether and other organic solvents.

In the manufacture of sausages such as raw-smoked sausages, the enzymatic composition is added into the raw materials during mixing thereof with salting ingredients. 100 g of the enzymatic agent are used per 100 kg of the raw materials. For a better distribution of the composition, it is advisable to introduce it into the raw materials in the form of a 10-20% aqueous solution. Thereafter, a stuff is made according to a given formulation which is then packed into an envelope. The stuffed loafs are subjected to shrinkage at a temperature of 2° to 6° C. under a high relative humidity conditions (about 96-98%) for 1 to 3 days. Thereafter, sausage loafs are smoked at a temperature of from 12° to 22° C. for a period of from 2 to 4 days and then dried at a temperature of not more than 15° C., preferably 12° C. while strictly controlling the value of relative humidity which should be gradually lowered by the end of drying. It is preferable that at the beginning of drying the relative humidity value be about 80% and at the end of drying,; about 75%. Duration of drying depends on the type of sausage and loaf diameter and ranges from 20 to 35 days.

Sausage products manufactured by this method have a dense consistency, clearly pronounced smoke smell and satisfy the requirements imposed on raw-smoked sausages.

EXAMPLE 2

The process is carried out in a manner similar to that described in the foregoing Example 1, except that use is made of 0.5 g of ox serum albumin and 4 g of hyaluronidase. There are obtained 4 g of an amorphous powder (the yield is 90%) of white color with a slight specific smell of raw meat, readily soluble in water at a pH within the range of from 2.0 to 8.5 and insoluble in ethanol, acetone, ether and other organic solvents.

The resulting enzymatic composition is useful in both wet and dry treatment of meat.

EXAMPLE 3

The process is conducted in a manner similar to that of Example 1 hereinabove, except that as the solvent use is made of ethanol in the amount of 6 volumes per 1 volume of the aqueous filtrate.

The thus-prepared enzymatic composition has the properties which are similar to those of the product described in Example 1 hereinbefore; it is useful in the manufacture of various sausage products.

EXAMPLE 4

The process is carried out as in Example 1, except that as the organic solvent for precipitation of the enzymatic agent use is made of ethylacetate in the amount of 5 volumes per 1 volume of the aqueous filtrate.

The thus-prepared enzymatic composition has properties similar to those described in the foregoing Example 1.

What is claimed is:

1. A method for preparing an enzymatic composition for accelerating the aging of meat comprising:
   (A) Separately dissolving 4 to 6 parts by weight hyaluronidase and 0.5 to 1.5 parts by weight serum albumin in water having a pH of from 2.0 to 2.5;
   (B) Mixing said solution of hyaluronidase with said solution of serum albumin, thereby obtaining a water soluble complex of hyaluronidase and said serum albumin in solution and suspended particles of unreacted ingredients;

(C) Separating the water soluble complex solution from the suspended unreacted ingredients;

(D) Cooling said separated water soluble complex solution to 4 to 6 degrees centigrade;

(E) Precipitating the cooled water soluble complex from aqueous solution by means of an organic solvent present in a volumetric ratio between said organic solvent and aqueous solution of from 4:1 to 10:1 respectively;

(F) Separating the precipitated complex from the liquid phase; and (G) Drying the separated precipitated complex successively with acetone and ethyl ether.

2. The method of claim 1 wherein mixing step (B) is effected at a temperature within the range of from 18° to 20° C. for a period of from 1 to 2 hours.

3. The method of claim 1 wherein the cooled solution of step (D) is gradually added to the organic solvent of step (E), said organic solvent being preliminarily cooled to not more than 10° C.

4. The method of claim 3 wherein the organic solvent of step (E) is preliminarily cooled to from 2° to 4° C.

5. The method of claim 1 wherein the organic solvent is acetone, ethyl acetate, ethanol, or another monohydric alcohol.

6. The method of claim 5 wherein the organic solvent is ethanol present in about 6 parts by volume per 1 part by volume of aqueous filtrate.

7. The method of claim 5 wherein the organic solvent is ethyl acetate present in about 5 parts by volume per 1 part by volume of aqueous filtrate.

8. The method of claim 1 wherein mixing step (B) is effected at a temperature within the range of from 18° to 20° C. for a period of from 1 to 2 hours; and the cooled solution of step (D) is gradually added to the organic solvent of step (E), said organic solvent being preliminarily cooled to from 2° to 4° C. and selected from the group consisting of acetone, ethyl acetate, ethanol, or another monohydric alcohol.

9. Meat or meat products treated with the composition prepared by the method of claim 1, by adding said composition in an amount of from about 0.05 to about 2 percent by weight of the meat or meat products.

* * * * *